US010947964B2

(12) United States Patent
Holzhausen et al.

(10) Patent No.: US 10,947,964 B2
(45) Date of Patent: Mar. 16, 2021

(54) SYSTEM AND METHOD FOR PRECISION FLUID DELIVERY

(71) Applicant: AAV LLC, Dover, DE (US)

(72) Inventors: Rudolf Holzhausen, Al Jasra (BH); John Earl Campbell, Jr., Birchwood, TN (US)

(73) Assignee: AAV LLC, Dover, DE (US)

( * ) Notice: Subject to any disclaimer, the term of this patent is extended or adjusted under 35 U.S.C. 154(b) by 368 days.

(21) Appl. No.: 15/905,430

(22) Filed: Feb. 26, 2018

(65) Prior Publication Data

US 2018/0363638 A1   Dec. 20, 2018

Related U.S. Application Data

(60) Provisional application No. 62/521,156, filed on Jun. 16, 2017.

(51) Int. Cl.
*F04B 43/12* (2006.01)
*A61M 5/142* (2006.01)
(Continued)

(52) U.S. Cl.
CPC ........... *F04B 43/1253* (2013.01); *A61D 7/00* (2013.01); *A61J 7/0053* (2013.01);
(Continued)

(58) Field of Classification Search
CPC .............. F04B 43/1253; F04B 43/1261; F04B 43/1269; F04B 43/12; F04B 43/1276; A61M 5/14232; A61D 7/00
See application file for complete search history.

(56) References Cited

U.S. PATENT DOCUMENTS 3,614,434 A * 10/1971 Horwitz .................... G01T 7/02
250/364
4,976,590 A * 12/1990 Baldwin ............. F04B 43/1253
417/477.3
(Continued)

FOREIGN PATENT DOCUMENTS

EP          2764881 A1    8/2014
WO     2007/002154 A2    1/2007
(Continued)

OTHER PUBLICATIONS

Screen captures from YouTube video clip entitled "Phillips Repeater Injector, Injection/Vaccination Equipment," 12 pages, uploaded on Sep. 20, 2011 by user "Cox Agri". Retrieved from Internet: <https://www.youtube.com/watch?v=dkP-MCZO2FM>.
(Continued)

*Primary Examiner* — Jenna Zhang
(74) *Attorney, Agent, or Firm* — Duane Morris LLP

(57) ABSTRACT

The present disclosure is directed to a robust system and method that delivers precise volumes of fluid, including weight-based fluid volumes (e.g., as prescribed by a medication dose), avoids the expenses and complexity associated with having multiples devices for cutaneous, subcutaneous, and oral administration, avoids the time-consuming cleaning associated with internal component contamination, and avoids the expenses and complications associated with human and mechanical error and failure, of prior art mass fluid delivery systems and methods.

20 Claims, 5 Drawing Sheets

(51) Int. Cl.
*A61D 7/00* (2006.01)
*F04B 49/06* (2006.01)
*F04B 49/20* (2006.01)
*A61J 7/00* (2006.01)
*A61M 5/168* (2006.01)
*F04B 15/02* (2006.01)

(52) U.S. Cl.
CPC ........ *A61M 5/14232* (2013.01); *A61M 5/168* (2013.01); *F04B 15/02* (2013.01); *F04B 49/065* (2013.01); *F04B 49/20* (2013.01); *A61M 2205/33* (2013.01); *A61M 2205/3365* (2013.01); *A61M 2205/50* (2013.01); *F04B 2205/14* (2013.01)

(56) References Cited

U.S. PATENT DOCUMENTS

| | | | |
|---|---|---|---|
| 7,056,307 B2 | 6/2006 | Smith et al. | |
| 2002/0188470 A1* | 12/2002 | Hogan | A61D 7/00 705/2 |
| 2004/0006309 A1* | 1/2004 | Rusnak | A61D 1/025 604/131 |
| 2004/0195382 A1* | 10/2004 | Anderson | B05B 12/00 239/525 |
| 2005/0025647 A1* | 2/2005 | Ortega | F04B 43/1253 417/477.1 |
| 2005/0182391 A1 | 8/2005 | Schiltges et al. | |
| 2006/0181695 A1 | 8/2006 | Sage, Jr. | |
| 2009/0157219 A1 | 6/2009 | Parker, Jr. et al. | |
| 2015/0170545 A1 | 6/2015 | Baker et al. | |
| 2016/0114104 A1 | 4/2016 | Hyde et al. | |

FOREIGN PATENT DOCUMENTS

| | | |
|---|---|---|
| WO | 2011/058194 A1 | 5/2011 |
| WO | 2012/109678 A2 | 8/2012 |
| WO | 2014/037331 A1 | 3/2014 |
| WO | 2016/077534 A1 | 5/2016 |
| WO | 2016/102619 A1 | 6/2016 |
| WO | 2016/202339 A1 | 12/2016 |

OTHER PUBLICATIONS

Screen captures from YouTube video clip entitled "Correct drenching technique—sheep worming," 5 pages, uploaded on Jul. 31, 2015 by user "AHDB Beef & Lamb". Retrieved from Internet: <https://www.youtube.com/watch?v=m0TFBU75DiM>.

* cited by examiner

SYSTEM AND METHOD FOR PRECISION FLUID DELIVERY

CROSS-REFERENCE TO RELATED APPLICATIONS

This application claims priority to U.S. Provisional Patent Application Ser. No. 62/521,156, filed on Jun. 16, 2017, the entirety of which is incorporated herein by reference.

FIELD

The present disclosure is generally directed to precision fluid delivery. More specifically, the present disclosure is directed to a portable electromechanical system including a rotary positive displacement pump driven by a motor, a microcontroller, and associated electronics; flexible tubing; a fluid reservoir; and a handheld applicator for cutaneously, subcutaneously, and/or orally delivering predetermined volumes of fluids of varying viscosities.

DESCRIPTION OF THE RELATED ART

Ranchers, pastoral farmers, and veterinarians are required to mass administer precise volumes of various types of medicament (e.g., a vaccine, an antiprotozoal, an antibiotic, a dip, a supplement, or combinations thereof) to large quantities of animals on an annual, semi-annual, or more frequent basis. They must also accurately track the medicament administration to each particular animal. Different medicaments may be required to be administered in different ways. For example, some medicaments must be delivered orally, others must be delivered cutaneously or dermally, and still others must be delivered subcutaneously or subdermally. Often, the volume of a particular medicament that must be delivered to a particular animal is based on the current weight of the particular animal. Several prior art devices are available for administering different types of medicaments in different ways.

Conventional technology used to subcutaneously vaccinate mass quantities of animals includes mechanically driven gun pumps. These mechanical pumps include a refillable, graduated chamber having a needle at one end (e.g., a syringe) for both subcutaneously administering the medicament to an animal and refilling the chamber from a bottle filled with the medicament. This chamber is operatively coupled to a retractable plunger. During a filling step, the plunger is manually retracted to draw medicament from the bottle into the chamber. During an administering step and responsive to a manual pull of a trigger of the pump, the plunger moves a preset amount to mechanically pump a preset dose of the medicament from the chamber and through the needle. A manually rotatable dial controls how far the plunger travels responsive to each trigger pull (and therefore controls the dose of medicament pumped through the needle).

The internal components of these mechanical pumps (plunger, dial, chamber, and needle) each contact or have a high risk of contacting the medicament, and thus the pump must be disassembled and cleaned before changing medicaments to avoid cross-contamination. These mechanical pumps also have a limited volume and must be refilled frequently. Additionally, because the pumps are actuated by manual trigger pulls, the ability to administer the medicament and the accuracy of administering the medicament is subject to mechanical error and failure and human error. For example, the plunger may stick rather than move the desired amount and therefore pump less than a full dose of medicament through the needle. Also, the repeated trigger pulls required to administer medicament to many animals in a short period of time is very tiring for a human operator (e.g., to the operator's grip), and could negatively impact the dose volume. This problem is exacerbated if the medicament has a relatively high viscosity, which makes it more difficult to pull the trigger and to pump the medicament through the gun pump.

Given the difficulty of subcutaneously administering high-viscosity medicaments, such as certain deworming/parasite control medications, a rancher, a pastoral farmer, or a veterinarian may purchase and use a different type of conventional mechanical pump to orally administer these higher viscosity medicaments. For example, conventional mechanically driven gun pumps to orally administer medicaments may be coupled to a medicament reservoir (e.g., a medicament-filled bag) by flexible plastic tubing that may be carried by the human operator including by strapping the reservoir to the operator's back. These conventional mechanically driven gun pumps are again manually actuated by a trigger to deliver a preset amount of medicament for oral delivery to an animal. Thus, these mechanical pumps suffer from the same contamination and mechanical and human fatigue problems identified above for subcutaneous-delivery mechanical pumps, especially as they are delivering a higher viscosity medicament.

Conventional technology used to treat mass quantities of animals cutaneously or dermally includes a technique known as dipping. A conventional delivery device includes a flexible chamber connected to a smaller diameter graduated cylinder with a simple pressure-operated valve disposed internally therebetween. During a chamber-filling step, the chamber is filled with medicament by the operator connecting a larger volume medicament-filled reservoir to the graduated cylinder; elevating the reservoir above the delivery device; and squeezing the chamber to open the valve and draw the medicament from the reservoir, through the cylinder, and into the chamber. This process is repeated until the chamber is filled with medicament and the larger volume reservoir is disconnected from the cylinder. The animal-to-be-treated is retained in a pen and physically rendered stationary. During an administering step, the operator rotates the delivery device such that the cylinder is above the restrained animal's skin and the chamber is above the cylinder; squeezes the chamber with one hand to open the valve and dispense medicament from the chamber, through the cylinder, and onto the skin of the animal; and then spreads the medicament onto the surrounding skin of the animal using his other hand. All of the components of this conventional technology are subject to contamination, and the technology is inaccurate, very tiring for a human operator, and has inherent risks of injury and stress to the animal.

The complex nature of the mass medicament administration process introduces many potential sources of error. Conventional technology used to administer the medicament renders the processes very tedious and time consuming. The failure to properly perform these processes may result in significant losses to the rancher or the pastoral famer as well as persons that provide goods and services to the ranchers, pastoral farmers, or animals, and persons that sell meat after these animals are slaughtered. There is therefore an increasing need for precision fluid delivery systems, devices, and methods that solve these problems.

SUMMARY

The present disclosure is directed to a robust system and method that delivers precise volumes of fluid, including weight-based fluid volumes (e.g., as prescribed by a medication dose), avoids the expenses and complexity associated with having multiples devices for cutaneous, subcutaneous, and oral administration, avoids the time-consuming cleaning associated with internal component contamination, and avoids the expenses and complications associated with human and mechanical error and failure, of prior art mass fluid delivery systems and methods.

In various embodiments, a portable, electromechanical device for dispensing fluid is provided. The device includes a housing, a rotary pump supported by the housing and including a plurality of rollers extending laterally from the housing and rotatable about an axis of rotation. The device also includes a motor operatively connected to the rotary pump to rotate the rollers relative to a tube guide and along a rotational path about the axis of rotation, the rotational path including an upper roller position and a lower roller position. The tube guide includes a tube contact surface, and the tube guide is attached to an external surface of the housing such that the tube contact surface is spaced a first distance from the upper roller position and a second distance greater than the first distance from the lower roller position. The first distance is configured to be smaller than the outer diameter of a flexible tube when such tube is disposed between the tube contact surface and a surface of one of the rollers in the upper roller position.

In some embodiments, the tube contact surface is curved. In some embodiments, the tube guide is movable relative to the external surface of the housing and relative to the rotary pump. In some embodiments, the device includes a controller operatively connected to the motor to control the motor. In some embodiments, the rotary pump includes a pump shaft, the rollers are rotatable with the pump shaft, the motor includes a motor output shaft operably connected to the pump shaft, and the controller is operatively connected to the motor to control a rotational speed of the motor shaft, which in turn controls a rotational speed of the pump shaft. In some embodiments, the controller is configured to control the motor based on a control input. In some embodiments, the control input is received via an input device. In some embodiments, the device is configured to be housed in a carrying container. In some embodiments, the device includes first and second connection blocks extending laterally from the housing and disposed on opposing sides of the rotary pump. In some embodiments, the first and second connection blocks are each configured to receive and secure a respective portion of a flexible tube when such tube is disposed between the tube contact surface and the plurality of rollers of the rotary pump.

In various embodiments, a portable system for dispensing fluid is provided. The system includes an electromechanical device. The electromechanical device includes a housing, and a rotary pump supported by the housing. The rotary pump includes a plurality of rollers extending laterally from the housing and rotatable about an axis of rotation. The electromechanical device also includes a motor operatively connected to the rotary pump to rotate the rollers relative to a tube guide and along a rotational path about the axis of rotation, the rotational path including an upper roller position and a lower roller position. The tube guide includes a tube contact surface. The tube guide is attached to an external surface of the housing such that the tube contact surface is spaced a first distance from the upper roller position and a second distance from the lower roller position, the second distance being greater than the first distance. The electromechanical device also includes a controller operatively connected to the motor to control the motor. The system also includes an applicator including an actuator movable between a rest position and an activated position. The actuator is communicatively connected to the controller to send a signal to the controller when the actuator is moved from the rest position to the activated position. The applicator also includes an applicator tip mounting device to which an applicator tip is removably attachable.

In some embodiments, the system includes a tube fluidically connectable to a fluid source and to the applicator tip mounting device and which is sized to fit between the rollers and the tube contact surface. In some embodiments, an outer diameter of the tube is larger than the first distance such that a roller in the upper roller position compresses the tube against the tube contact surface when the tube is disposed between the rollers and the tube contact surface. In some embodiments, the outer diameter of the tube is smaller than the second distance such that a roller in the lower roller position does not compress the tube against the tube contact surface when the tube is disposed between the rollers and the tube contact surface. In some embodiments, the electromechanical device, the fluid source, and at least a part of the tube, are configured to be housed in a carrying container. In some embodiments, the application tip is configured to deliver fluid from the application tip mounting device to a subject cutaneously, subcutaneously, orally, or combinations thereof.

In some embodiments, the applicator defines an inner channel therethrough. In some embodiments, the applicator includes an inlet connector in fluid communication with the applicator tip mounting device via the inner channel, and the tube is fluidically connectable to the inlet connector to fluidically connect the tube with the applicator tip mounting device via the inner channel. In some embodiments, the inner channel is sized to receive part of the tube such that the tube can directly fluidically connect with the applicator tip mounting device. In some embodiments, the pump includes a pump shaft, the rollers are rotatable with the pump shaft, the motor includes a motor output shaft, the motor output shaft is operably connected to the pump shaft, and the controller is operatively connected to the motor to control a rotational speed of the motor shaft, which in turn controls a rotational speed of the pump shaft. In some embodiments, the controller is configured to control the motor based on a control input. In some embodiments, the control input is received via an input device. In some embodiments, the controller is configured to control the motor based on the control input responsive to receipt of the signal from the actuator.

In various embodiments, a method of dispensing fluid is provided. The method includes receiving a control input at a controller operatively connected to a rotary pump of a portable, electromechanical device. The method also includes, based on the control input, determining, at the controller, the quantity of revolutions of the rotary pump about an axis of rotation required to dispense a predetermined volume of fluid from a tip of an applicator fluidically connected to a fluid source with a flexible tube. The rotary pump is supported by a housing of the electromechanical device, and includes a plurality of rollers extending laterally from the housing. The plurality of rollers are configured to rotate relative to a tube guide and along a rotational path about the axis of rotation, the rotational path including an upper roller position and a lower roller position. The method also includes receiving, at the controller, a signal indicating activation of an actuator of the applicator. The method further includes, in response to receiving the signal, automatically rotating the rotary pump about the axis of rotation until the determined quantity of revolutions is achieved. In some embodiments, the rotation of the rotary pump periodically compresses a portion of the flexible tube between a tube contact surface of the tube guide and successive ones of the rollers in the upper roller position as the plurality of rollers rotate along the rotational path to dispense the predetermined volume of fluid from the tip of the applicator.

In some embodiments, the rotary pump includes a pump shaft, the plurality of rollers are rotatable with the pump shaft, the motor includes a motor output shaft, and the motor output shaft is operably connected to the pump shaft. In some embodiments, the controller is operatively connected to the motor to control a rotational speed of the motor output shaft. In some embodiments, the method includes controlling a rotational speed of the pump shaft by controlling, at the controller, the rotational speed of the motor output shaft. In some embodiments, the method includes, based on the control input, determining, at the controller, the quantity of revolutions of the motor output shaft required to cause the rotary pump to rotate the required quantity of revolutions. In some embodiments, in response to receiving the signal indicating activation of the actuator of the applicator, the method includes automatically rotating the motor output shaft until the determined quantity of revolutions is achieved. In some embodiments, the method includes receiving another control input at the controller. In some embodiments, the method also includes, based on the another control input, determining, at the controller, the predetermined volume of fluid.

In various embodiments, a method of dispensing fluid is provided. The method includes disposing a portion of a flexible tube between one or more rollers of a plurality of rollers of a rotary pump of a portable, electromechanical device and a tube guide attached to an external surface of a housing of the electromechanical device. The plurality of rollers extend laterally from the housing of the electromechanical device and are configured to rotate relative to the tube guide about an axis of rotation and along a rotational path including an upper roller position and a lower roller position. The method includes fluidically connecting a tip of an applicator to a fluid source with the flexible tube. The method also includes receiving a signal indicating activation of an actuator of the applicator at a controller operatively connected to the rotary pump. The method further includes, in response to receiving the signal, automatically rotating the plurality of rollers along the rotational path until a predetermined volume of fluid is dispensed from the tip of the applicator. In some embodiments, the rotation of the plurality of rollers periodically compresses a portion of the flexible tube between a tube contact surface of the tube guide and successive ones of the rollers in the upper roller position as the plurality of rollers rotate along the rotational path.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

DETAILED DESCRIPTION OF THE EXAMPLES

In some embodiments, a system for precisely delivering fluids includes a mobile electromechanical device including a rotary positive displacement pump driven by a motor, a microcontroller, and associated electronics; flexible disposable tubing; a fluid reservoir; and a handheld applicator for delivering predetermined volumes of fluids of varying viscosities and for various applications. The inventor has determined that the solutions described herein provide accurate dosage; weight-regulated dosage; radio-frequency identification (RFID (or bar code, quick-response (QR) code, or other subject identifying data) readability (e.g., for chipped animals); and recording functionality that avoid errors associated with missed doses or inadequate dosage in conventional technology.

Figure 1:
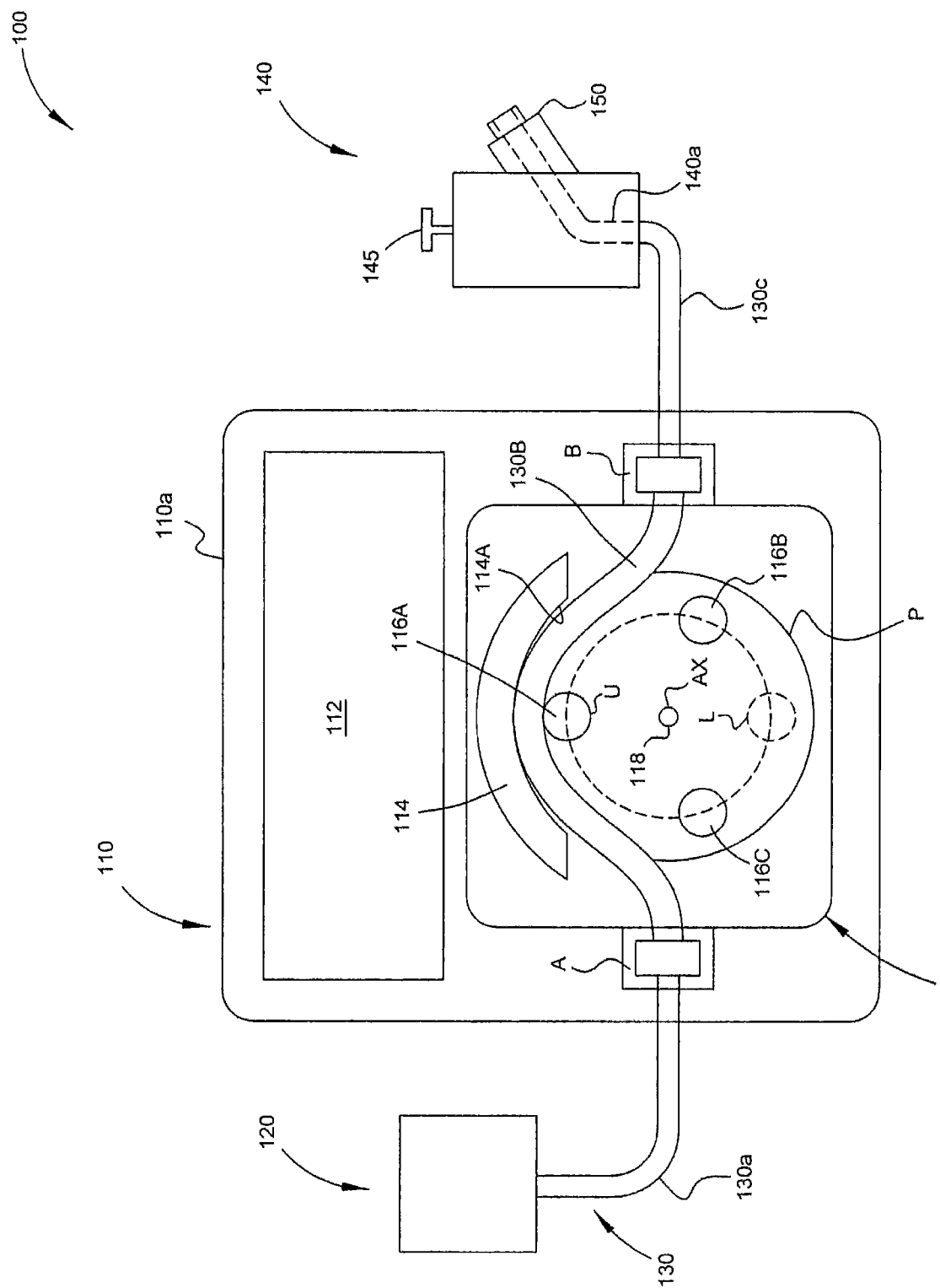
FIG. 1 is a simplified pictorial representation of one example embodiment of a system of the present disclosure.

Referring now to FIG. 1, a simplified pictorial representation of the system 100 of one embodiment of the present disclosure is provided. The system 100 includes an electromechanical device 110 fluidically connectable to a fluid source 120 and to an applicator 140 via a flexible tube 130 and configured to pump fluid from the fluid source 120 through the flexible tube 130 and to the applicator 140 to dispense the fluid, as described in detail below.

Figure 2:
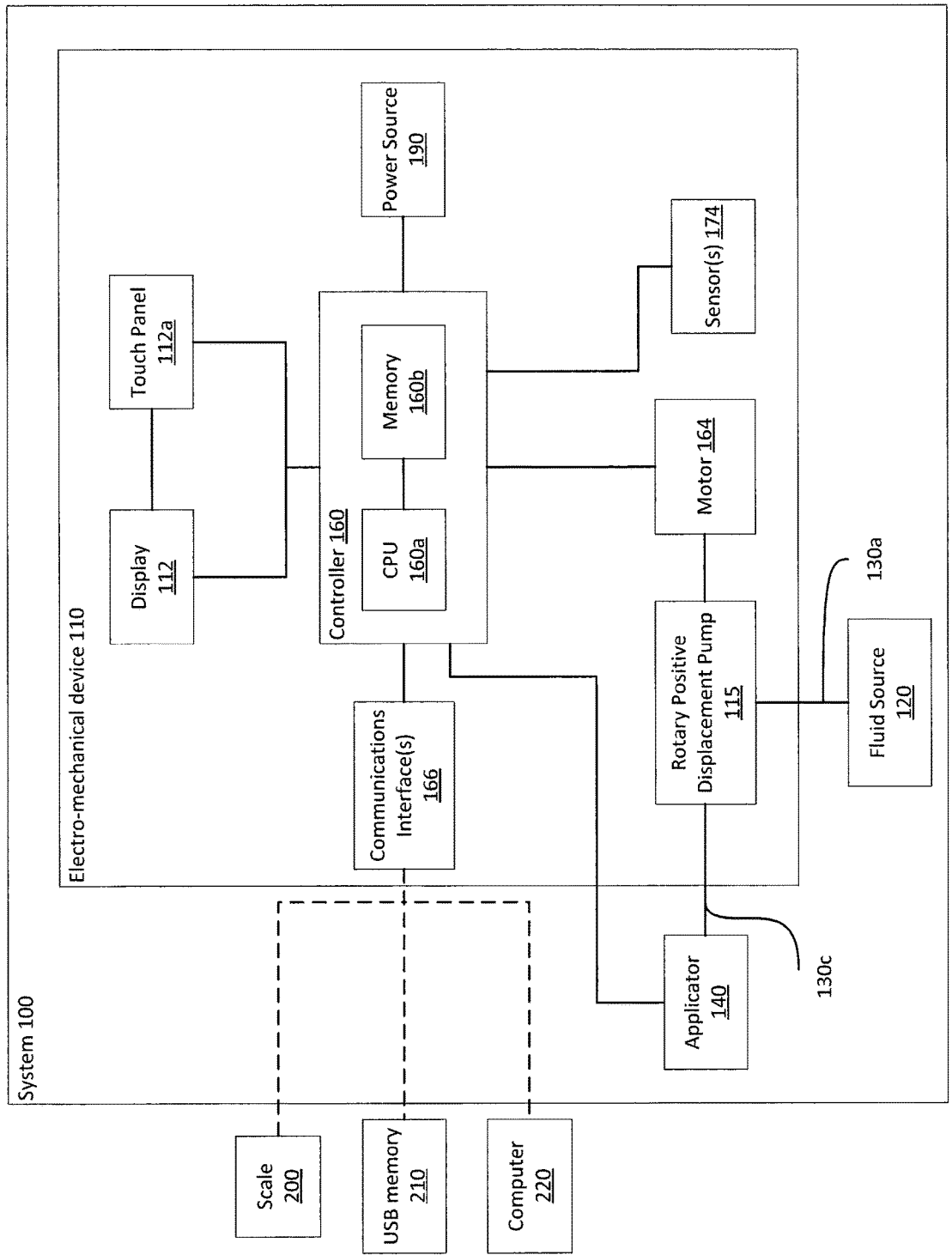
FIG. 2 is a block diagram illustrating certain components of the system of FIG. 1.
Figure 3:
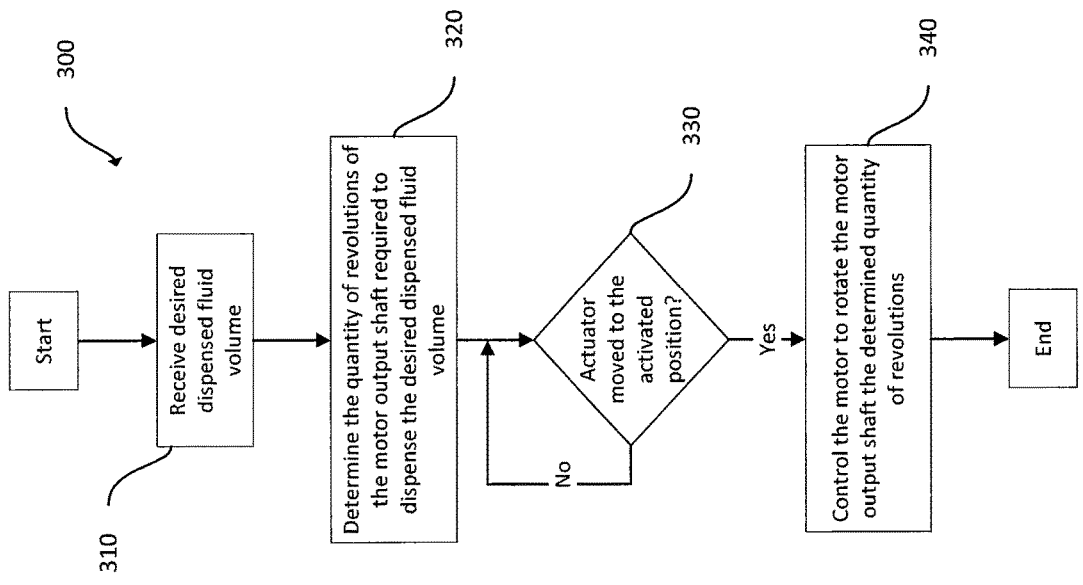
FIG. 3 is a flowchart of an example process of operating the system of FIG. 1 in a manual mode.

As best shown in FIGS. 1-3, the electromechanical device 110 includes a display 112, a touch panel 112a, a pump casing including a tube guide 114, a rotary positive displacement pump 115, a first connection block A, a second connection block B, a controller 160, a motor 164, one or more communications interfaces 166, one or more sensors 174, and a power source 190.

The controller 160 includes a central processing unit (CPU) 160a communicatively connected to a memory 160b. The CPU 160a is configured to execute program code or instructions stored on the memory 160b to control operation of various components of the electromechanical device 110. The CPU 160a may be a microprocessor with digital signal processing (DSP) functionality; a content-addressable memory; a digital-signal processor; an application-specific integrated circuit; a field-programmable gate array; any suitable programmable logic device, discrete gate, or transistor logic; discrete hardware components; or any combination of these. The CPU 160a may also be implemented as a combination of these devices, such as a combination of a digital signal processor and a microprocessor, a plurality of microprocessors, or one or more microprocessors in conjunction with a digital signal processor core.

The memory 160b is configured to store, maintain, and provide data as needed to support the functionality of the electromechanical device 110. For instance, in various embodiments, the memory stores program code or instructions executable by the CPU 160a to control operation of the electromechanical device 110. The memory 160 includes any suitable data storage device or devices, such as volatile memory (e.g., random-access memory, dynamic random-access memory, or static random-access memory); non-volatile memory (e.g., read-only memory, mask read-only memory, programmable read-only memory, erasable programmable read-only memory, electrically erasable programmable read-only memory); and/or non-volatile random-access memory (e.g., flash memory, solid-state storage). The memory 160b may be removable from the electromechanical device 110 and replaceable.

The display 112 includes, without limitation: a liquid-crystal display (LCD), a display based on light-emitting diodes (LEDs), a display based on a plurality of organic LEDs, a display based on polymer LEDs, a display based on a plurality of surface-conduction electron emitters, a display including a projected or reflected image, a plasma display, a cathode-ray tube display, or any other suitable display mechanism. The controller 160 is operatively coupled to the display 112 to control the display 112 to display images and video responsive to signals received from the controller 160. In this example embodiment, the display 112 has a diagonal dimension of about 130 millimeters, though the display may be any suitable size in other embodiments.

The touch panel 112a is configured to enable an operator to provide different inputs to the controller 16Q. The touch panel 112a is overlaid atop (or otherwise coupled to or associated with) the display 112 and enables an operator to provide various inputs to the controller 160 by interacting with a graphical user interface (GUI) by performing any of a variety of different touch operations (e.g., touching and releasing the touch panel, swiping the touch panel, or double tapping the touch panel) with a finger or a compatible stylus, depending on the embodiment. The touch panel 112a is configured to send the coordinate data of the detected location of the input touch operation to the controller 160, which is configured to control the electromechanical device 110 to perform an operation responsive to the received touch input. In this example embodiment, the touch panel 112a is a capacitive touch panel, though the electromechanical device 110 may include any suitable type of touch panel (such as a resistive touch panel).

The motor 164 is any suitable type of motor, such as a brushless direct-current (DC) electric motor, including a motor output shaft (not shown). The controller 160 is operatively coupled to the motor 164 to control the output of the motor 164, such as the rotational velocity of the motor output shaft. In various embodiments, the motor 164 is configured such that the ramp-up time of the motor 164, which is the time it takes for the motor to increase its rotational velocity from zero to a desired rotational velocity, is negligible.

The rotary positive displacement pump 115 is any suitable rotary positive displacement pump, such as a rotoflex pump or a peristaltic pump. The rotary positive displacement pump 115 includes a rotor 117 fixedly connected to a shaft 118. A plurality of rollers 116a, 116b, and 116c are attached to the rotor 117 and are circumferentially arranged around the shaft 118. The motor output shaft is operatively connected to the shaft 118 to rotate the shaft 118—and therefore the rotor 117 and the rollers 116 attached thereto—about an axis of rotation AX that is coaxial with a longitudinal axis of the shaft 118. As the motor 164 causes the pump shaft 118 to rotate, the rollers 116a, 116b, and 116c travel along a circular path of rotation P between an upper position U (where roller 116a is located in FIG. 1) and a lower position L (shown in phantom in FIG. 1).

The pump 115 is at least partially housed within a cuboid (or any other suitably shaped) pump casing or housing (not labeled) that, in this embodiment, has a depth of about 40 millimeters (though the pump casing may have any other suitable depth in other embodiments). The pump casing includes a tube guide 114 that includes a curved tube-contact surface 114a. The tube guide 114 is positioned relative to the pump 115 such that the tube-contact surface 114a is spaced apart from the rollers 116 when the rollers 116 are in the upper position U of the path of rotation P. Additionally, the tube guide 114 is positioned relative to the pump 115 such that the distance separating the tube-contact surface 114a aid the rollers 116 when in the upper position U of the path of rotation P is smaller than the outer diameter of the second portion of flexible tubing 130b (described below). In some embodiments, the tube guide 114 is movable or removable relative to the pump casing to enable the tube guide 114 to move to enable installation of the second flexible tube portion 130.

The communications interface(s) 166 is(are) suitable wired or wireless communications interfaces configured to establish and facilitate communication between the controller 160 and one or more external devices. These may be any suitable types of communications interfaces, such as: (1) a universal serial bus (USB) interface configured to receive a USB connector and communicatively connect the controller 160 to the device connected to that USB connector (such as a scale 200 or a USB memory device 210) to enable the controller 160 to communicate with that device; (2) a Wi-Fi network interface configured to communicatively connect the controller 160 to a wireless network—such as the Internet or a local area network—to enable the controller 160 to communicate with other devices (such as a computer 220) on that network; (3) a wired network interface configured to receive a network cable connector and to communicatively connect the controller 160 to a wireless network—such as the Internet or a local area network—to enable the controller 160 to communicate with other devices on that network; (4) a cellular network interface configured to communicatively connect the controller 160 to a cellular network to enable the controller 160 to communicate with other devices connected to the cellular network; (5) a Bluetooth interface configured to wirelessly pair the controller 160 to another Bluetooth-enabled device to enable the controller 160 to communicate with the other Bluetooth-enabled device; (6) a radio-frequency identification (RFID) interface configured to read RFID tags; (7) a radio-frequency (RF) interface configured to communicatively connect the controller 160 with another device via radio signals; and (8) a near-field communications interface (NFC) configured to communicatively connect the controller 160 with another device via an NFC protocol.

The electromechanical device 110 may include or be communicatively connectable to (via the communications interface(s) 166) any other suitable input devices configured to enable an operator to provide an input to the controller 160. These input devices may include a button (such as a hard key or a programmable soft key), a mouse, a trackball, a microphone, or a device configured to receive tactile inputs.

The power source 190 includes a battery, such as a lithium-polymer battery, a lithium-ion battery, a nickel-metal-hydride battery, a nickel-cadmium battery, or any other suitable rechargeable or non-rechargeable power supply sufficient to power the components of the electromechanical device 110. In other embodiments, the power source is not part of the electromechanical device 110, but is instead an external power source (such as an alternating-current power source) to which the electromechanical device 110 is electrically connectable to power the components of the electromechanical device 110.

The first and second connection blocks A and B, respectively, are suitable devices configured to receive and hold the flexible tubing 130a, 130b, and 130c in place during operation of the electromechanical device 110.

The flexible tube 130 includes first, second, and third flexible tube portions 130a, 130b, and 130c. The flexible tube portions may be formed from any suitable material, such as silicon or plastic, and may be disposable. In this example embodiment, the flexible tube portion 130b has a larger inner diameter than the flexible tube portions 130a and 130c (which have the same inner diameter in this example embodiment, but may have different inner diameters in other embodiments). Accordingly, in this example embodiment, the flexible tube portions 130a, 130b, and 130c are discrete components mechanically and fluidically connected to one another via suitable connectors (not shown). In this example embodiment, the connector that mechanically and fluidically connects the flexible tube portion 130a to the flexible tube portion 130b is attachable to the first connection block A, and the connector that mechanically and fluidically connects the flexible tube portion 130b to the flexible tube portion 130c is attachable to the first connection block B. In other embodiments, the flexible tube portions 130a, 130b, and 130c are integrally formed as one unitary component. In further embodiments, some, all, or none of the components may have the same inner diameter. In some embodiments, the flexible tube 130 includes one or more check valves to prevent backflow of the fluid from the flexible tube 130 to the fluid source 120.

The sensor(s) 174 include any suitable sensors configured to sense environmental characteristics (such as air pressure or temperature) and to send signals representing those sensed characteristics to the controller 160.

The above-described components are either attached (or attachable) to or (partially or completely) enclosed within an electromechanical device housing 110a. In this example embodiment, the electromechanical device housing 110a is a cuboid (or any other suitable shape) having a width of about 150 millimeters, a height of about 200 millimeters, and a depth of about 50 millimeters, (though these dimensions may be other values in other embodiments). In this example embodiment, the electromechanical device, including a power source 190 such as a lithium-polymer battery, weighs about 2 pounds.

The fluid source 120 may include any suitable container or other element filled with fluid, such as a fluid reservoir, fluid bag, or a bottle. The fluid source 120 includes an outlet connector (such as a quick-connect connector, not shown) fluidically connectable to the flexible tube 130.

The applicator 140 includes an applicator tip mounting device (not shown) fluidically connectable to the flexible tube 130. The applicator 140 also includes an actuator 145 movable between a rest position and an activated position. As shown in FIG. 1, handheld applicator 140 includes an actuator 145 such as, for example, a button configured to be depressed by a human operator. In various embodiments, a human operator indicates the readiness state for the predetermined volume of fluid to be delivered by operating the actuator (e.g. depressing the button). The applicator 140 is communicatively connected to the controller 160 via the actuator 145 such that the actuator 145 can send a suitable signal to the controller 160 responsive to being moved from the rest position to the activated position. In various embodiments, the motor 164 (e.g. a stepper motor) rotates at an approximately constant velocity with negligible ramp up time. In various embodiments, one or more of the algorithms programmed into a controller 160 are executed to calculate the time to "turn on" the stepper motor. In various embodiments, this information, and other information (e.g. fluid identification data, weight of subject to be treated, identification of subject to be treated (e.g. from RFID and data-bases), real-time environmental factors (e.g. pressure, air, temperature) at treating location, etc.) is provided as an input to controller 160. In various embodiments, one or more algorithms programmed into controller 160 control the input to the motor 164. which then controls the rotation of the pump 115 to deliver a desired set volume of fluid (or dose) from the tip 150 of handheld applicator 140.

The applicator 140 defines an internal channel 140a that enables the applicator tip mounting device to be fluidically connected to the flexible tube 130. In this embodiment, the applicator 140 includes an inlet connector (such as a quick-disconnect connector, not shown) to which the flexible tube 130 is removably connectable. Here, when the flexible tube 130 is connected to the inlet connector, fluid can flow from the flexible tube 130 through the internal channel 140a and to the applicator tip mounting device. Thus, the flexible tube 130 is in fluid communication with the applicator tip mounting device via the internal channel 140a. In various embodiments, the internal channel 140a is lined or otherwise formed from stainless steel or any other suitable material.

In other embodiments, the internal channel 140a is sized and otherwise configured to receive part of the flexible tube 130 such that the flexible tube 130 can directly fluidically connect to the applicator tip mounting device. That is, in these embodiments, when the flexible tube is connected to the applicator tip mounting device, fluid can flow from the flexible tube 130 to the applicator tip mounting device. The fluid does not contact the internal channel in these embodiments.

Although not shown here, in other embodiments the applicator 140 includes a grip sized, shaped, and otherwise configured to receive the fingers of a human operator.

The applicator tip mounting device is configured such that any of a variety of different applicator tips 150 can be removably mounted thereto. Each applicator tip 150 is configured to dispense the fluid. When an applicator tip 150 is mounted to the applicator tip mounting device, the applicator tip 150 is in fluid communication with the flexible tube 130—either via the internal channel 140a or directly (as described above)—to receive fluid therefrom and dispense that fluid.

In various embodiments, the applicator tip 150 is configured to removably attach to the applicator tip mounting device of the applicator 140 to enable oral fluid delivery, cutaneous fluid delivery, and/or subcutaneous fluid delivery to a subject, such as an animal. The fluid may be, for example, a vaccine, an antiprotozoal, an antibiotic, a dip, a supplement, or any other medicament or combinations thereof. In some embodiments, the fluid may include a fertilizer, and the applicator tip 150 may be configured to deliver (e.g., spray) the fluid onto individual plants or as a wholesale application. In some embodiments, the fluid may include a pesticide, and the applicator tip 150 may be configured to deliver (e.g., spray) the fluid onto individual plants, grass or as a wholesale application. In some embodiments, the fluid may include an herbicide or fungicide, and applicator tip 150 may be configured to deliver (e.g., spray) the fluid onto individual plants, grass or as a wholesale application. In some embodiments, the fluid may include a slurry of water and ice melt, and applicator tip 150 may be configured to deliver (e.g., spray) the fluid onto sidewalks, driveways, rooftops, etc.

To dispense fluid stored in the fluid store 120 via the applicator 140, an operator fluidically connects: (1) the free end of the first portion 130a of the flexible tube 130 to the outlet connector (not shown) of the fluid store 120; and (2) the free end of the third portion 130c of the flexible tube 130 to the inlet connector (not shown) of the applicator 140. The operator then secures the flexible tube 130 to the first and second connection blocks A and B (as described above) and positions part of the second portion 130*b* of the flexible tube 130 between the tube-contact surface 114*a* of the tube guide 114 and the rollers 116*a*, 116*b*, and 116*c* of the pump 115. Put differently, the second portion 130*b* of the flexible tubing 130 is positioned such that the pump 115 (via the rollers 116*a*, 116*b*, and 116*c*) and the tube guide 114 (via the tube-contact surface 114*a*) are operatively coupled to the second portion 130*b* to pump fluid through the flexible tube 130. Although not shown here, a retaining element (such as a plate) retains the second portion 130*b* of the flexible tube 130 in place in the direction into and out of the page (i.e., the direction of the axis AX of the shaft 118) such that the rollers 116 contact the second portion 130*b* of the flexible tube 130 as they rotate.

In operation, as the motor output shaft of the motor 164 rotates and causes the shaft 118 to rotate, the rollers 116*a*, 116*b*, and 116*c* periodically compress and release the portion of the second portion 130*a* of the flexible tube 130 against and from the tube-contact surface 114*a* of the tube guide 114. The compression forces the fluid contained in the flexible tube 130 to be pumped through the second portion 130*b* of the flexible tube 130 and toward the third portion 130*c* of the flexible tube 130. The release step causes the compressed portion of the second portion 130*b* of the flexible tube 130 to re-open (upon further rotation of the rollers 116*a*, 116*b*, and 116*c* along the path P), and induces fluid to flow into the flexible tubing 130 from the fluid source 120.

In various embodiments, the fluid source 120 and the electromechanical device 110 are configured to be housed in a carrying container, such as a back or front pack, for convenient handling. In various embodiments, the carrying container is configured to be custom form fitting to the shape of the fluid source 120 and the electromechanical device 110 (including the pump 115).

The system is configured to eliminate the need for time-consuming cleaning associated with internal component contamination of prior art fluid delivery devices. In various embodiments, the only components of the system 100 that come in contact with the fluid transported therethrough are the fluid source 120, the flexible tube 130, and the applicator tip 150. In other embodiments (such as that shown in FIGS. 1 and 2), the only components of system 100 that come in contact with fluid transported therethrough are the fluid source 120, the flexible tubing 130, the internal channel 140*a* of the applicator 140, and the applicator tip 150. The flexible tubing 130 and/or the applicator tip 150 may be disposable. The applicator tip 150 and, if in contact with fluid, the internal channel 140*a* of the applicator 140 are configured to be cleaned in a simple manner, such as by flushing with clean water. In various embodiments, such components may be sanitized by any suitable sanitizer, such as betadine.

FIG. 3 is a flowchart of an example process 300 of operating the system 100 in a manual operating mode. In various embodiments, a set of instructions stored in the memory 160*b* and executed by the processor 160*a* represents the process 300. Although the process 300 is described with reference to the flowchart shown in FIG. 3, many other processes of performing the acts associated with this illustrated process 300 may be employed. For example, the order of certain of the illustrated blocks or diamonds may be changed, certain of the illustrated blocks or diamonds may be optional, or certain of the illustrated blocks or diamonds may not be employed.

The process 300 begins with the operator using the touch panel to instruct the controller (e.g. controller 160) to operate in a manual operating mode. The controller receives a desired dispensed fluid volume, as block 310 indicates. The controller may receive the desired dispensed fluid volume via operator input via the touch panel or in any other suitable manner. The controller determines the quantity of revolutions of the motor output shaft (or, for example, the pump shaft) required to dispense the desired dispensed fluid volume from the applicator tip, as block 320 indicates. The controller does so via one or more of a plurality of algorithms that correlate the desired dispensed fluid volume with a quantity of revolutions of the motor output shaft (or, for example, the pump shaft). These algorithms may directly or indirectly use any or all of the following as inputs: the inner diameter of the second portion of the flexible tube; the diameters of the rollers; the quantity of rollers; the radial distance of the rollers from the axis of the pump shaft; the distance between tube-contact surface of the tube guide and the rollers at the upper position; the identity of the fluid (and therefore its characteristics, including, for example, viscosity); the temperature of the fluid; a viscosity preset value of the fluid; the volume of fluid required to be delivered for a subject; any gear reduction present between and operatively coupling the motor output shaft and the shaft of the pump; real-time environmental factors sensed by the sensors (e.g., air pressure and temperature); length of a third portion of the flexible tube; real-time mechanical factors (e.g. the latency or ramp-up time of the motor, rotational friction, friction within the flexible tube) or estimates of the same; revolution step or increment size (and therefore number of steps or increments per revolution (e.g. per revolution of the motor output shaft of the pump)).

For example, at block 320, the controller (e.g. controller 160) may determine the quantity of revolutions, or fractions of a revolution, of motor output shaft 118 (or pump shaft 118) of pump 115 that is required to dispense the desired dispensed fluid volume (block 310) from applicator tip 150, based on several fixed variables and a viscosity preset value based on the viscosity of the fluid to be delivered to the subject (e.g. in units of centipoise (cP), millipascal-seconds (mPa-s), pascal-seconds (Pa-s), etc.) and the mechanical characteristics of the electromechanical devices. In various embodiments, the viscosity preset value for a particular fluid is the volume of the fluid delivered in one 360-degree rotation (i.e. one revolution) of a shaft of a pump of a particular electromechanical device (e.g. in units of mL/revolution). In various embodiments, the controller may determine a preset calibration value for an electro-mechanical device (e.g. electro-mechanical device 110) using a plurality of constants (e.g. ten fixed values) input and stored in a suitable storage device of electromechanical device 110 (e.g. memory 160*b*, USB memory 210, etc.). In various embodiments, the plurality of constants may include one or more of an inner diameter of the second portion of the flexible tube (e.g. 130*b*); an outer diameter of the second portion of the flexible tube (e.g. 130*b*); the diameters of the rollers (e.g. 116*a*-116*c*); the quantity of rollers (e.g. 116*a*-116*n*); the radial distance of the rollers (e.g. 116*a*-116*n*) from the axis of the pump shaft (e.g. 118); the distance between tube-contact surface of the tube guide (e.g. 114) and the rollers at the upper position (e.g. U); gear reduction present between and operatively coupling the motor output shaft and the pump shaft (e.g. 118); length of a third portion of the flexible tube (e.g. 130c); real-time mechanical factors (e.g. the latency or ramp-up time of the motor, rotational friction, friction within a flexible tube) or estimates of the same; and the revolution step or increment size (and therefore number of steps or increments per revolution (e.g. per revolution of the motor output shaft of the pump, per revolution of the pump shaft)). In various embodiments, the controller may compensate for determined or estimated values of one or more real-time mechanical factors (e.g. the latency or ramp-up time of the motor, rotational friction, friction within flexible tube) by adding or subtracting a predetermined number of revolution steps or increments.

In various embodiments, the controller (e.g. controller 160) may use the plurality of constants to determine the preset calibration value of the electro-mechanical device (electro-mechanical device 110). In various embodiments, the controller stores the determined preset calibration value in a suitable storage device of electromechanical device 110 (e.g. memory 160b). In various embodiments, the controller (e.g. controller 160) uses the preset calibration value, the viscosity of the particular fluid to be delivered to the subject, and other variables such as, for example the temperature of the fluid, to determine the viscosity preset value for the particular fluid. In various embodiments, the controller (e.g. controller 160) may be programmed such that water ($H_2O$) at 25 degrees Celsius has a viscosity preset value of 0 mL/revolution for an electro-mechanical device (e.g. electro-mechanical 110). In various embodiments, controller 160 may determine that other fluids (e.g. medicaments) have a determined viscosity preset value higher or lower than 0 mL/revolution for the electromechanical device. In various embodiments, the controller stores the respective determined viscosity preset values of various fluids (e.g. various medicaments) in a suitable storage device of electromechanical device 110 (e.g. memory 160b). In various embodiments, the controller (e.g. controller 160) uses the viscosity preset value for the particular fluid to be delivered to a particular subject to determine the number of revolutions (i.e. one 360 degree rotation), e.g. or fractions of a revolution, of the pump (e.g. of pump shaft (e.g. pump shaft 118) or of the motor output shaft of a pump (e.g. pump 115)) of an electro-mechanical device (electro-mechanical device 110) required to deliver the desired dispensed fluid volume to the subject.

For example, the desired dispensed fluid volume of a particular fluid for a particular subject (DDF) may be 10 mL. The determined viscosity preset value (VPV) for the particular fluid at 25 degrees Celsius within the tubing of the electro-mechanical device may be 4 mL/revolution. The determined total steps or increments per revolution (TSPR) for the pump of the electromechanical device may be 200 (or a step/increment size of 1.8 degrees). The controller may determine the total volume of the particular fluid dispensed per step/increment (FPS) as (FPS=VPV/FSPR)=(4/200) =0.02 mL per step/increment. The controller may determine the total steps/increments required to deliver the desired dispensed fluid volume of the particular fluid from the applicator tip of the electro-mechanical device (TSDDF) to the subject as (DDF/FPS)=(10 mL/0.02 mL per step)=500 steps. The controller may determine the number of revolutions required to deliver the desired dispensed fluid volume to the subject as (TSDDF/TSPR)=(500 steps/200 steps per revolution)=2.5 revolutions.

The controller monitors for receipt of a signal from the actuator that the actuator has been moved to the activated position, as diamond 330 indicates. After receiving the signal, the controller controls the motor to rotate the motor output shaft the determined quantity of revolutions, as block 340 indicates. As explained above, this rotation of the motor output shaft causes the pump shaft to rotate, thereby causing the pump rollers to periodically compress and release the flexible tube in a manner that pumps the desired dispensed fluid volume out of the applicator tip.

Figure 4:
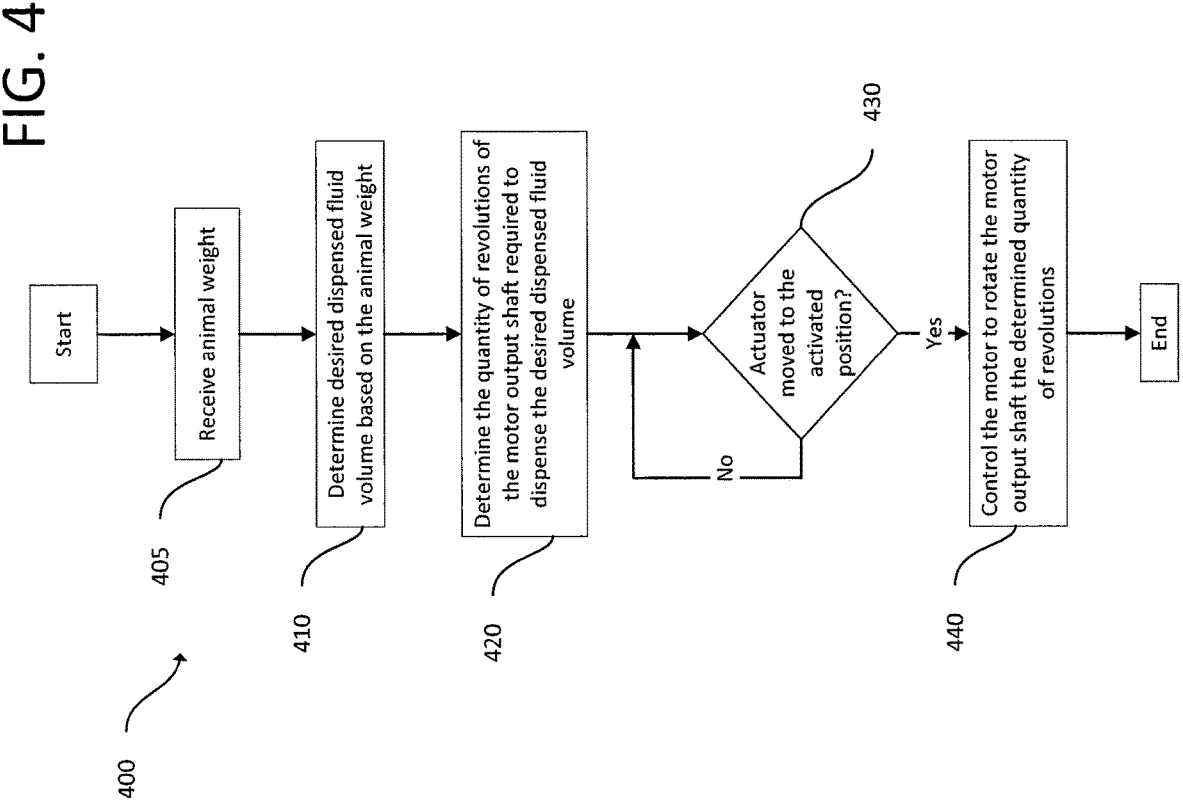
FIG. 4 is a flowchart of an example process of operating the system of FIG. 1 in an automatic mode.

FIG. 4 is a flowchart of an example process 300 of operating the system 100 in an automatic operating mode. In various embodiments, a set of instructions stored in the memory 160b and executed by the processor 160a represents the process 400. Although the process 400 is described with reference to the flowchart shown in FIG. 4, many other processes of performing the acts associated with this illustrated process 400 may be employed. For example, the order of certain of the illustrated blocks or diamonds may be changed, certain of the illustrated blocks or diamonds may be optional, or certain of the illustrated blocks or diamonds may not be employed.

The process 400 begins with the operator using the touch panel to instruct the controller to operate in an automatic operating mode and communicatively connecting the controller to the scale. The controller receives, via the scale, an animal weight, as block 405 indicates. The controller then determines a desired dispensed fluid volume based on the animal weight, as block 410 indicates. Blocks 420, diamond 430, and block 440 then proceed as described above for block 320, 330, and 340. The process 400 thus eliminates the need for the operator to manually determine an input a desired dispensed fluid volume, instead enabling the controller to determine that value based on the animal's weight and one or more stored correlations between the animal's weight, a particular fluid, and a desired dispensed fluid volume.

In other embodiments, the controller 160 is configured to calculate the quantity of revolutions of the pump 115 required to deliver the desired dispensed fluid volume from the applicator tip 150 and then determine (via suitable algorithms stored on the memory 160b) the quantity of revolutions of the motor output shaft required to cause the pump 115 to rotate the required quantity of revolutions.

In various embodiments, the internal diameter of the flexible tube 130 is approximately constant throughout such that the fluid volume pumped through the flexible tube 130 with each revolution (or partial revolution) of pump 115 is approximately constant. In some embodiments, the internal diameter of the second portion of the flexible tube 130b is approximately constant throughout such that the fluid volume pumped through the second portion of the flexible tube 130b with each revolution (or partial revolution) of pump 115 is approximately constant.

In certain embodiments in which the electromechanical device 110 includes an RFID reader, the system 100 is configured to provide accurate recording of which subject was dosed, when it was dosed, and by how much it was dosed to allow the human operator the capability to review that data and ensure that all subjects were treated properly. In various embodiments, the system 100 is configured to receive, retrieve, and store in memory historical treatment data (e.g., data in electronic medical records, data in medical history, etc.) received via one of the communications interfaces 166 from external devices and/or databases subject identification data (e.g., subject descriptive data (e.g., images, color, markings); microchip ID; name; and date of birth). In various embodiments, the system 100 may be configured to transmit information, such as dose volume, dose type, time of dose administration, location of dose administration, dosed subject identification data (e.g., subject descriptive data received via another communications interface and dosed subject weight data) via the communications interface 166 for external recording of historical treatment data (e.g., data in electronic medical records, data in medical history, etc.)

In various embodiments, graphical user interface of display 112 includes an interface configured to permit a human operator to securely login to, and be authenticated by, the system, such as via password, speech, or biometrics.

Figure 5:
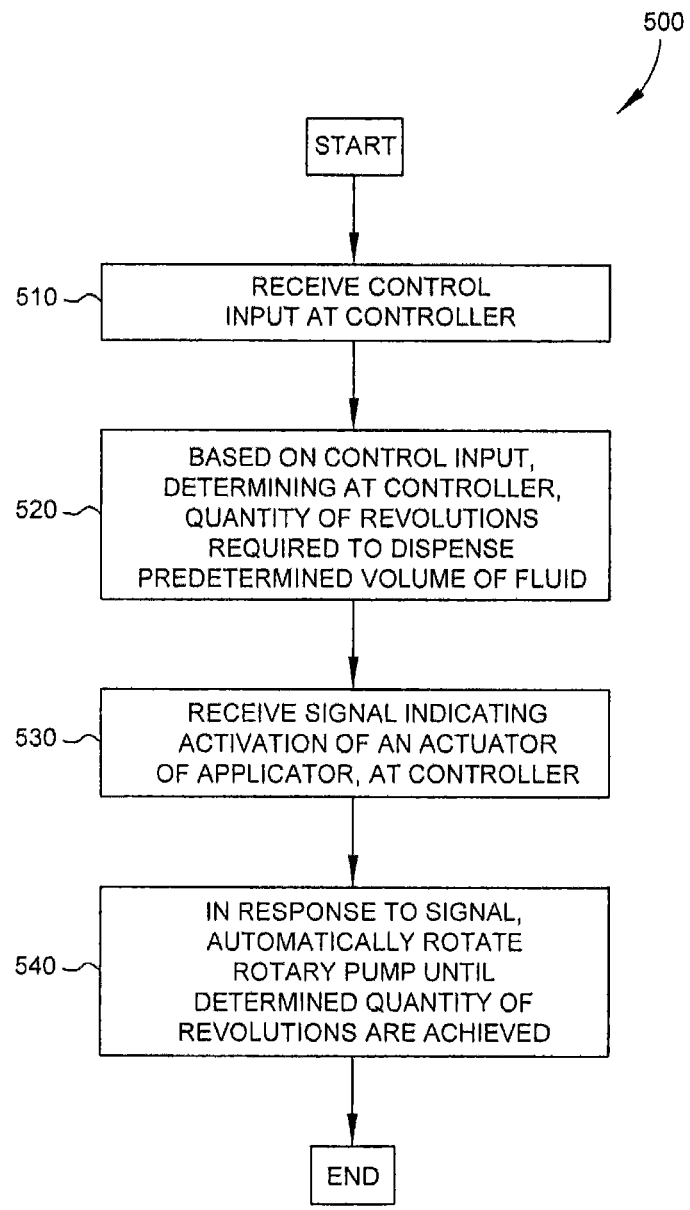
FIG. 5 is a flow chart of an example embodiment of a method of the present disclosure.

FIG. 5 is a flow chart of an example embodiment 500 of the method of the present disclosure. At block 510, a control input is received at a controller (e.g. 160) operatively connected to a rotary pump (e.g. 115) of a portable, electromechanical device (e.g. 110). At block 520, based on the control input, the quantity of revolutions of the rotary pump (e.g. 115), about an axis of rotation (e.g. AX), that is required to dispense a predetermined volume of fluid from a tip (e.g. 150) of an applicator (e.g. 140) fluidically connected to a fluid source (e.g. 120) with a flexible tube (e.g. 130) is determined at the controller (e.g. 160). In various embodiments, the rotary pump (e.g. 115) is supported by a housing (e.g. 110a) of the electromechanical device (e.g. 110), and includes a plurality of rollers (e.g. 116a-116c) extending laterally from the housing (e.g. 110a). In various embodiments, the plurality of rollers (e.g. 116a-116c) are configured to rotate relative to a tube guide (e.g. 114) and along a rotational path (e.g. P) about the axis of rotation (e.g. AX), the rotational path (e.g. P) including an upper roller position (e.g. U) and a lower roller position (e.g. L). At block 530, a signal, indicating activation of an actuator (e.g. 145) of the applicator (e.g. 140), is received at the controller (e.g. 160). At block 540, in response to receiving the signal, the rotary pump (e.g. 115) is automatically rotated about the axis of rotation (e.g. AX) until the determined quantity of revolutions is achieved. In some embodiments, the rotation of the rotary pump (e.g. 115) periodically compresses a portion of the flexible tube (e.g. 130) between a tube contact surface of the tube guide (e.g. 114) and successive ones of the rollers (e.g. 116a, 116b, 116c) in the upper roller position (e.g. U) as the plurality of rollers (e.g. 116a-116c) rotate along the rotational path (e.g. P) to dispense the predetermined volume of fluid from the tip (e.g. 150) of the applicator (e.g. 140).

In some embodiments, the rotary pump (e.g. 115) includes a pump shaft (e.g. 118). In some embodiments, the plurality of rollers (e.g. 116a-116c) are rotatable with the pump shaft (e.g. 118). In some embodiments, a motor (e.g. 164) includes a motor output shaft, and the motor output shaft is operably connected to the rotary pump shaft (e.g. 118). In some embodiments, the controller (e.g. 160) is operatively connected to the motor (e.g. 164) to control a rotational speed of the motor output shaft. In some embodiments, a method includes controlling a rotational speed of the rotary pump shaft (e.g. 118) by controlling, at the controller (e.g. 160), the rotational speed of the motor output shaft. In some embodiments, a method includes, based on the control input (e.g. received at block 510), determining, at the controller, the quantity of revolutions of the motor output shaft required to cause the rotary pump (e.g. 115) to rotate the required quantity of revolutions. In some embodiments, in response to receiving the signal indicating activation of the actuator of the applicator (e.g. at block 530), a method includes automatically rotating the motor output shaft until the determined quantity of revolutions is achieved. In some embodiments, a method includes receiving another control input at the controller (e.g. 160). In some embodiments, a method also includes, based on the another control input, determining, at the controller (e.g. 160), the predetermined volume of fluid that is required to dispense from a tip (e.g. 150) of an applicator (e.g. 140) fluidically connected to a fluid source (e.g. 120) with a flexible tube (e.g. 130).

Figure 6:
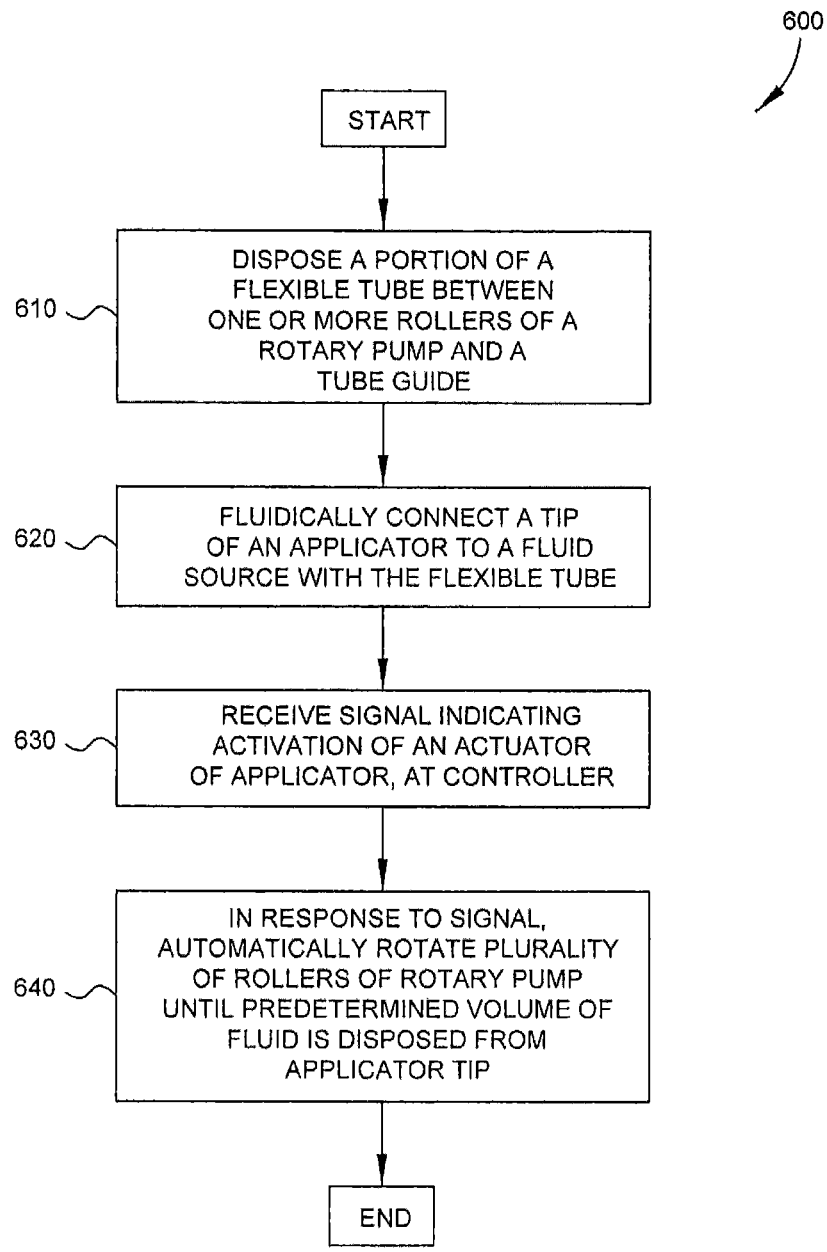
FIG. 6 is a flow chart of an example embodiment of a method of the present disclosure.

FIG. 6 is a flow chart of an example embodiment 600 of the method of the present disclosure. At block 610, a portion of a flexible tube (e.g. 130) is disposed between one or more rollers (e.g. 116a, 116b, 116c) of a plurality of rollers (e.g. 116a-116c) of a rotary pump (e.g. 155) of a portable, electromechanical device (e.g. 110) and a tube guide (e.g. 114) attached to an external surface of a housing (e.g. 110a) of the electromechanical device (e.g. 110). In various embodiments, the plurality of rollers (e.g. 116a-116c) extend laterally from the housing (e.g. 110a) of the electromechanical device (e.g. 110) and are configured to rotate relative to the tube guide (e.g. 114) about an axis of rotation (e.g. AX) and along a rotational path (e.g. P) including an upper roller position (e.g. U) and a lower roller position (e.g. L). At block 620, a tip (e.g. 150) of an applicator (e.g. 160) is fluidically connected to a fluid source (e.g. 120) with the flexible tube (e.g. 130). At block 630, a signal, indicating activation of an actuator (e.g. 145) of the applicator (e.g. 154), is received at a controller (e.g. 160) operatively connected to the rotary pump (e.g. 115). At block 640, in response to receiving the signal, the plurality of rollers (e.g. 116a-116c) are automatically rotated along the rotational path (e.g. P) until a predetermined volume of fluid is dispensed from the tip (e.g. 150) of the applicator (e.g. 160). In some embodiments, the rotation of the plurality of rollers (e.g. 116a-116c) periodically compresses a portion of the flexible tube (e.g. 130) between a tube contact surface of the tube guide (e.g. 114) and successive ones of the rollers (e.g. 116a, 116b, 116c) in the upper roller position (e.g. U) as the plurality of rollers (e.g. 116a-116c) rotate along the rotational path (e.g. P).

Thus, the present disclosure is directed to an inexpensive, portable, accurate fluid delivery system and method that avoids fluid contact with electromechanical device components; limits fluid contact to inexpensive and disposable components and/or easily accessible and cleanable components; avoids mechanical and operator fatigue; is accurate, effective, and operator-friendly with fluids of various types and viscosities; is highly scalable to mass administration of medicament; and is easily adapted to administer fluids orally, cutaneously, and subcutaneously.

It may be emphasized that the above-described embodiments are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure. Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal that is generated to encode information for transmission to suitable receiver apparatus for execution by a computer. The computer readable medium can be a machine-readable storage device, a machine-readable storage substrate, a memory device, a composition of matter affecting a machine-readable propagated signal, or a combination of one or more of them.

The term "circuitry" encompasses all apparatus, devices, and machines for processing data, including by way of example a programmable processor, a computer, or multiple processors or computers. The circuitry can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The invention claimed is:

1. A portable system for dispensing fluid, the system comprising:
   an electromechanical device comprising:
      a housing;
      a rotary pump supported by the housing and comprising a plurality of rollers that extend laterally from the housing and that are rotatable about an axis of rotation;
      a motor operatively connected to the rotary pump to rotate the plurality of rollers relative to a tube guide and along a rotational path about the axis of rotation, the rotational path including an upper roller position and a lower roller position;
      the tube guide comprising a tube contact surface, the tube guide attached to an external surface of the housing such that the tube contact surface is spaced a first distance from the upper roller position and a second distance from the lower roller position, the second distance being greater than the first distance;
      a memory configured to store:
         a plurality of values for particular mechanical characteristics of the electromechanical device;
         a respective viscosity preset value for each of a plurality of different fluid types, wherein each respective viscosity preset value is a respective volume of a respective one of the plurality of fluid types dispensed in one 360-degree revolution about the axis of rotation of the rotary pump when each of the plurality of particular mechanical characteristic values is held constant; and
         a calibration viscosity preset value for a predetermined fluid type at a predetermined fluid temperature;
      a non-transitory computer readable medium comprising instructions stored thereon that, when executed by a processor, cause the processor to:
         receive the calibration viscosity preset value for the electromechanical device;
         determine, relative to the received calibration viscosity preset value and with the plurality of particular mechanical characteristic values of the electromechanical device held constant, the respective viscosity preset value for each of the plurality of different fluid types;
         during an operation to dispense fluid to a subject:
            receive a weight value for the subject and an identification of one of the plurality of different fluid types to be dispensed to the subject;
            determine a desired fluid volume of the identified fluid type to be dispensed to the subject based on the received weight value for the subject; and
            determine a number of revolutions of the rotary pump based on the determined respective viscosity preset value for the identified fluid type to be dispensed to the subject, and the determined desired fluid volume of the identified fluid type to be dispensed to the subject; and
      a controller operatively connected to the motor to control the motor based on the determined number of revolutions; and an applicator comprising:

an actuator movable between a rest position and an activated position, the actuator communicatively connected to the controller to send a signal to the controller when the actuator is moved from the rest position to the activated position, wherein the signal indicates the determined desired fluid volume of the identified fluid type is ready to be dispensed to the subject; and a removably attachable applicator tip.

2. The system of claim 1, wherein the electromechanical device is further configured to house a flexible tube; and wherein, during operation, in response to the actuator sending the signal, the controller is configured to control the rotation of the plurality of rollers for the determined number of revolutions along the rotational path to dispense the determined desired fluid volume of the identified fluid type from the removably attachable applicator tip by periodic compression of a portion of the flexible tube between the tube contact surface of the tube guide and the respective one of the plurality of rollers in the upper roller position and periodic decompression of the portion of the flexible tube as each respective one of the plurality of rollers rotates into and out from the upper roller position.

3. The system of claim 2, wherein the determined number of revolutions comprises a fraction of the 360-degree revolution along the rotational path.

4. The system of claim 2, wherein the applicator defines an inner channel therethrough, wherein the applicator further comprises an inlet connector configured to operatively connect to an end of the flexible tube, and wherein, during operation, the fluid source is in fluid communication with the removably attachable applicator tip via the flexible tube and the inner channel.

5. The system of claim 2, wherein the applicator defines an inner channel therethrough, wherein the inner channel is configured to house another portion of the flexible tube such that, during operation, the removably attachable applicator tip is fluidically connected to the fluid source via the flexible tube and, during operation, the identified fluid type only contacts the fluid source, the flexible tube, and the removably attachable applicator tip.

6. The system of claim 2, wherein the electromechanical device, the fluid source, and, during operation, at least a the portion of the flexible tube, are configured to be housed in a carrying container.

7. The system of claim 1, wherein the electromechanical device further comprises:
an RFID reader configured to receive a signal indicating an RFID tag of the subject;
wherein, during operation, the controller is configured to provide, for storage in the memory, a time of administration of the determined desired fluid volume of the identified fluid type, the RFID tag of the subject, and the determined desired fluid volume of the identified fluid type dispensed from the removably attachable applicator tip.

8. The system of claim 1, wherein the pump comprises a pump shaft, the plurality of rollers are rotatable with the pump shaft, the motor is operably connected to the pump shaft, and the controller is operatively connected to the motor to control a rotational speed of the motor, which in turn controls a rotational speed of the pump shaft, in response to receipt of the signal from the controller when the actuator is moved from the rest position to the activated position.

9. The system of claim 1, wherein the removably attachable applicator tip is configured to deliver fluid from the applicator to the subject cutaneously, subcutaneously, orally, or through combinations thereof.

10. The system of claim 1, wherein the instructions, when executed by the processor, further cause the processor to:
receive an identification of another one of the plurality of different fluid types to be dispensed to the subject;
determine a desired fluid volume of the identified another fluid type to be dispensed to the subject based on the received weight value for the subject; and
determine a number of revolutions of the rotary pump based on the determined respective viscosity preset value for the identified another fluid type to be dispensed to the subject, and the determined desired fluid volume of the identified another fluid type to be dispensed to the subject.

11. The system of claim 1, wherein the plurality of particular mechanical characteristic values comprise a value for a step size or a total number of steps per revolution of the rotary pump; and wherein the instructions stored on the non-transitory computer readable medium, when executed by the processor, further cause the processor to:
determine a per-step volume of the identified fluid type to be dispensed to the subject based on the determined respective viscosity preset value for the identified fluid type to be dispensed to the subject, and the stored value for the total number of steps per revolution, or revolution step size, of the rotary pump; and
determine a total number of steps to dispense the determined desired fluid volume of the identified fluid type to the subject based on the determined per-step volume of the identified one fluid type to be dispensed to the subject, and the determined desired fluid volume of the identified one fluid type to be dispensed to the respective subject; and
wherein the instruction to cause the processor to determine the number of revolutions of the rotary pump further causes the processor to use the determined total number of steps to dispense the determined desired fluid volume of the identified one fluid type to the subject, and the stored value for the total number of steps per revolution, or revolution step size, of the rotary pump.

12. A computer-implemented method of dispensing a particular fluid volume to a subject, the method comprising:
storing, in a memory:
a plurality of values for particular mechanical characteristics of an electromechanical device;
a respective viscosity preset value for each of a plurality of different fluid types, wherein each respective viscosity preset value is a respective volume of a respective one of the plurality of fluid types dispensed in one 360-degree revolution about an axis of rotation of a rotary pump of the electromechanical device when each of the plurality of particular mechanical characteristic values is held constant; and
a calibration viscosity preset value for a predetermined fluid type at a predetermined fluid temperature;
receiving the calibration viscosity preset value for the electromechanical device;
determining, relative to the received calibration viscosity preset value and with the plurality of particular mechanical characteristic values of the electromechanical device held constant, the respective viscosity preset value for each of the plurality of different fluid types;
during an operation to dispense fluid to a subject:

receiving a weight value of a subject, and an identification of one of the plurality of different fluid types to be dispensed to the subject;

determining a desired fluid volume of the identified fluid type to be dispensed to the subject based on the received weight value for the subject;

based on the determined respective viscosity preset value for the identified fluid type to be dispensed to the subject and the determined desired fluid volume of the identified fluid type to be dispensed to the subject, determining a number of revolutions of the rotary pump required to dispense the determined desired fluid volume of the identified fluid type from a removably attachable applicator tip of an applicator;

receiving a signal indicating activation of an actuator of the applicator;

in response to receiving the signal, rotating a pump shaft of the rotary pump for the determined number of revolutions, the electromechanical device further comprising:

a tube guide; and a plurality of rollers rotatable with the pump shaft along a rotational path, the rotational path including an upper roller position relative to the tube guide; and dispensing the determined desired fluid volume of the identified fluid type from the removably attachable applicator tip during the rotating step, wherein the applicator is fluidically connected to a fluid source via a flexible tube, and wherein, as each respective one of the plurality of rollers rotates into and out from the upper roller position during the rotating step, a portion of the flexible tube is periodically compressed between a surface of the tube guide and a surface of a respective one of the plurality of rollers in the upper roller position to pump fluid of the identified fluid type within the flexible tube toward the applicator, and periodically decompressed to draw fluid of the identified fluid type into the flexible tube from the fluid source.

13. The method of claim 12, further comprising: storing a time of administration of the determined desired fluid volume, an identifier of the subject, and the determined desired fluid volume of the identified fluid type dispensed from the applicator.

14. The method of claim 12, wherein a user may provide one or more inputs to a controller by interacting with a graphical user interface, and wherein the graphical user interface includes an interface configured to permit the user to securely login to, and be authenticated by, the electromechanical device via one or more of a password, speech, or biometric input.

15. The method of claim 12, wherein the applicator defines an inner channel therethrough, and wherein the inner channel is configured to house another portion of the flexible tube such that, during operation, the removably attachable applicator tip is fluidically connected to the fluid source via the flexible tube and, during operation, the fluid of the identified fluid type only contacts the fluid source, the flexible tube, and the removably attachable applicator tip.

16. The method of claim 12, wherein the stored plurality of mechanical characteristic values comprises at least two of: a diameter of the portion of the flexible tube; a diameter of the plurality of rollers; a quantity of the plurality of rollers; a radial distance of the plurality of rollers from an axis of rotation of the pump shaft; a distance between the surface of the tube guide and a roller of the plurality of rollers in the upper roller position; a length of the portion of the flexible tube; an estimate of rotational friction; an estimate of friction within the flexible tube; a revolution step size of the rotary pump; and a total number of steps per revolution of the rotary pump.

17. A portable system for dispensing fluid without contamination, the system comprising:

a fluid source;

an electromechanical device comprising:

a housing;

a rotary pump supported by the housing and comprising a plurality of rollers that extend laterally from the housing and that are rotatable about an axis of rotation;

a motor operatively connected to the rotary pump to rotate the plurality of rollers relative to a tube guide and along a rotational path about the axis of rotation, the rotational path including an upper roller position and a lower roller position;

the tube guide comprising a tube contact surface, the tube guide attached to an external surface of the housing such that the tube contact surface is spaced a first distance from the upper roller position and a second distance from the lower roller position, the second distance being greater than the first distance, and wherein the electromechanical device is configured to house a flexible tube and to dispose the flexible tube at least partially between the tube guide and the rotary pump;

a memory configured to store:

a plurality of values for particular mechanical characteristics of the electromechanical device;

a respective viscosity preset value for each of a plurality of different fluid types, wherein each respective viscosity preset value is a respective volume of a respective one of the plurality of fluid types dispensed in one 360-degree revolution about the axis of rotation of the rotary pump when each of the plurality of particular mechanical characteristic values is held constant; and a calibration viscosity preset value of a predetermined fluid type at a predetermined fluid temperature;

a non-transitory computer readable medium comprising instructions stored thereon that, when executed by a processor, cause the processor to:

receive the calibration viscosity preset value for the electromechanical device;

determine, relative to the received calibration viscosity preset value and with the plurality of particular mechanical characteristic values held constant, the respective viscosity preset value for each of the plurality of different fluid types;

during an operation to dispense fluid to a subject:

receive a desired fluid volume for a particular one fluid type of the plurality of different fluid types to be dispensed to a subject; and determine a number of revolutions of the rotary pump based on the determined viscosity preset value for the particular fluid type to be dispensed to the subject, and the received desired fluid volume of the particular fluid type to be dispensed to the subject;

a controller operatively connected to the motor to control the motor based on the determined number of revolutions; and an applicator defining an inner channel therethrough and comprising a removably attachable applicator tip, wherein the inner channel is configured to house a portion of the flexible tube such that, during operation, the removably attachable applicator tip is fluidically connected to the fluid source, and wherein, during operation, fluid of the particular fluid type to be dispensed to the subject only contacts the fluid source, the flexible tube, and the removably attachable applicator tip, the applicator further comprising:

an actuator movable between a rest position and an activated position, the actuator communicatively connected to the controller to send a signal to the controller when the actuator is moved from the rest position to the activated position, wherein the signal indicates the received desired fluid volume of the particular fluid type is ready to be dispensed to the subject; and wherein the removably attachable applicator tip is configured to dispense fluid of the particular fluid type to the subject cutaneously, subcutaneously, orally, or through combinations thereof.

18. The system of claim 17, wherein, during operation, in response to the actuator sending the signal, the controller is configured to control the rotation of the plurality of rollers for the determined number of revolutions along the rotational path to dispense the received desired fluid volume of the particular fluid type from the removably attachable applicator tip by periodic compression of another portion of the flexible tube between the tube contact surface of the tube guide and the respective one of the plurality of rollers in the upper roller position and decompression of the another portion of the flexible tube as each respective one of the plurality of rollers rotates into and out from the upper roller position.

19. The system of claim 17, wherein the instructions, when executed by the processor, further cause the processor to:

receive a weight value for the subject and an identification of the particular fluid type to be dispensed to the subject; and determine the desired fluid volume of the particular fluid type to be dispensed to the subject based on the received weight value for the subject.

20. The system of claim 17, wherein the stored plurality of mechanical characteristic values comprises at least two of: a diameter of the plurality of rollers; a quantity of the plurality of rollers; a radial distance of the plurality of rollers from the axis of rotation of the pump shaft; a distance between the tube contact surface and a roller of the plurality of roller in the upper roller position; an estimate of rotational friction; a revolution step size of the rotary pump; a total number of steps per revolution of the rotary pump; and a latency or ramp-up time of the motor.

* * * * *